US009553984B2

(12) United States Patent
Krause et al.

(10) Patent No.: US 9,553,984 B2
(45) Date of Patent: Jan. 24, 2017

(54) SYSTEMS AND METHODS FOR REMOTELY TUNING HEARING DEVICES

(75) Inventors: Lee S. Krause, Indialantic, FL (US);
Rahul Shrivastav, Gainsville, FL (US);
Bonny Banerjee, Palm Bay, FL (US);
Alice E. Holmes, Gainesville, FL (US)

(73) Assignees: UNIVERSITY OF FLORIDA RESEARCH FOUNDATION, INC., Gainesville, FL (US); COCHLEAR LIMITED, Macquarie University (AU)

(*) Notice: Subject to any disclaimer, the term of this patent is extended or adjusted under 35 U.S.C. 154(b) by 1634 days.

(21) Appl. No.: 12/748,819

(22) Filed: Mar. 29, 2010

(65) Prior Publication Data

US 2010/0232613 A1 Sep. 16, 2010

Related U.S. Application Data

(63) Continuation-in-part of application No. 11/421,889, filed on Jun. 2, 2006, now abandoned, which is a (Continued)

(51) Int. Cl.
*H04R 29/00* (2006.01)
*H04M 3/42* (2006.01)
(Continued)

(52) U.S. Cl.
CPC ............ *H04M 3/42391* (2013.01); *A61N 1/08* (2013.01); *A61N 1/36032* (2013.01);
(Continued)

(58) Field of Classification Search
CPC ... H04R 25/70; H04R 27/505; H04R 2499/11; H04R 2225/39; H04R 2225/55; H04R 2225/67; G10L 25/00; G10L 25/69; A61N 1/08; A61N 1/37264; A61N 1/36032; H04M 3/26; H04M 3/42391; H04M 3/493; H04M 1/2474; H04M 1/6061; H04M 1/72591; H04M 7/006
(Continued)

(56) References Cited

U.S. PATENT DOCUMENTS 4,049,930 A 9/1977 Fletcher et al.
4,327,252 A 4/1982 Tomatis
(Continued)

FOREIGN PATENT DOCUMENTS

EP 1519625 3/2005
JP 2002-291062 10/2002
(Continued)

OTHER PUBLICATIONS

Fujisaki et al. "Auditory Perception of Duration of Speech and Non-Speech Stimuli," 1973, pp. 45-64.
(Continued)

*Primary Examiner* — Xu Mei
(74) *Attorney, Agent, or Firm* — Merchant & Gould P.C.

(57) ABSTRACT

A method of tuning a hearing device includes sending a test signal to a model of a hearing device that may be remote from the actual hearing device being tuned. The test signal is encoded by the model and sent to the hearing device being tuned. The user of that hearing device sends a response signal based at least in part on the encoded test signal. This response is received and compared to the original test signal. Thereafter, an operational parameter is sent to the hearing device based on the comparison.

26 Claims, 13 Drawing Sheets

Related U.S. Application Data continuation-in-part of application No. 10/872,313, filed on Jun. 18, 2004, now Pat. No. 7,206,416.

(60) Provisional application No. 61/164,450, filed on Mar. 29, 2009, provisional application No. 60/492,103, filed on Aug. 1, 2003.

(51) Int. Cl.

| | | |
|---|---|---|
| *A61N 1/08* | (2006.01) | |
| *A61N 1/36* | (2006.01) | |
| *A61N 1/372* | (2006.01) | |
| *H04M 3/26* | (2006.01) | |
| *G10L 25/69* | (2013.01) | |
| *G10L 21/06* | (2013.01) | |
| *H04M 1/247* | (2006.01) | |
| *H04M 1/60* | (2006.01) | |
| *H04M 1/725* | (2006.01) | |
| *H04M 3/493* | (2006.01) | |
| *H04M 7/00* | (2006.01) | |
| *H04R 25/00* | (2006.01) | |

(52) U.S. Cl.
CPC .......... *A61N 1/37264* (2013.01); *H04M 3/26* (2013.01); *H04R 25/70* (2013.01); *G10L 25/69* (2013.01); *G10L 2021/065* (2013.01); *H04M 1/2474* (2013.01); *H04M 1/6016* (2013.01); *H04M 1/72591* (2013.01); *H04M 3/493* (2013.01); *H04M 7/006* (2013.01); *H04M 2201/39* (2013.01); *H04M 2207/18* (2013.01); *H04R 25/505* (2013.01); *H04R 2225/55* (2013.01); *H04R 2225/67* (2013.01); *H04R 2499/11* (2013.01)

(58) Field of Classification Search
USPC .... 381/60, 312, 315, 56, 58; 379/1.01, 1.03, 379/22, 22.02, 27.03, 21, 26.01, 27.01–27.02; 73/585; 600/559
See application file for complete search history.

(56) References Cited

U.S. PATENT DOCUMENTS

| | | | | |
|---|---|---|---|---|
| 4,953,112 | A | * 8/1990 | Widin et al. | ...................... 703/6 |
| 5,008,942 | A | 4/1991 | Kikuchi | |
| 5,785,661 | A | 7/1998 | Shennib | |
| 5,944,672 | A | * 8/1999 | Kim et al. | .................... 600/559 |
| 6,035,046 | A | 3/2000 | Cheng et al. | |
| 6,036,496 | A | * 3/2000 | Miller et al. | .................. 434/156 |
| 6,118,877 | A | 9/2000 | Lindemann et al. | |
| 6,446,038 | B1 | 9/2002 | Bayya et al. | |
| 6,684,063 | B2 | 1/2004 | Berger et al. | |
| 6,763,329 | B2 | 7/2004 | Brandel et al. | |
| 6,823,171 | B1 | 11/2004 | Kaario | |
| 6,823,312 | B2 | 11/2004 | Mittal et al. | |
| 6,913,578 | B2 | 7/2005 | Hou | |
| 6,914,996 | B2 | 7/2005 | Takeda | |
| 7,206,416 | B2 | 4/2007 | Krause et al. | |
| 2002/0120440 | A1 | 8/2002 | Zhang | |
| 2002/0138272 | A1 | 9/2002 | Bennett et al. | |
| 2003/0007647 | A1 | 1/2003 | Nielsen et al. | |
| 2007/0286350 | A1 | 12/2007 | Krause et al. | |
| 2010/0056950 | A1 | 3/2010 | Banerjee et al. | |
| 2010/0056951 | A1 | 3/2010 | Banerjee et al. | |
| 2010/0246837 | A1 | 9/2010 | Krause et al. | |

FOREIGN PATENT DOCUMENTS

| | | |
|---|---|---|
| WO | WO-98/44762 | 10/1998 |
| WO | WO-99/31937 | 6/1999 |
| WO | WO-01/84538 | 11/2001 |
| WO | WO-2004/080532 | 9/2004 |
| WO | WO-2005/062766 | 7/2005 |
| WO | WO-2007/030402 | 3/2007 |
| WO | WO-2008/081446 | 7/2008 |

OTHER PUBLICATIONS

Runkle et al. "Active Sensory Tuning for Immersive Spatialized Audio," ICAD, 2000, 4 pages.
International Search Report for PCT Appl. No. PCT/US04/19843, mailed Mar. 22, 2006, 2 pages.
Written Opinion for PCT Appl. No. PCT/US04/19843, mailed Mar. 22, 2006, 5 pages.
Examination Report for European Patent Appl. No. 04755788.9, mailed Nov. 18, 2009, 4 pages.
International Search Report for PCT Appl. No. PCT/US09/55348, mailed Apr. 23, 2010, 5 pages.
Written Opinion for PCT Appl. No. PCT/US09/55348, mailed Apr. 23, 2010, 10 pages.
International Search Report for PCT Appl. No. PCT/US2010/029020, mailed Jul. 12, 2010, 3 pages.
Written Opinion for PCT Appl. No. PCT/US2010/029020, mailed Jul. 12, 2010, 7 pages.
International Search Report for PCT Appl. No. PCT/US2010/029021, mailed Jul. 16, 2010, 3 pages.
Written Opinion for PCT Appl. No. PCT/US2010/029021, mailed Jul. 16, 2010, 7 pages.

* cited by examiner

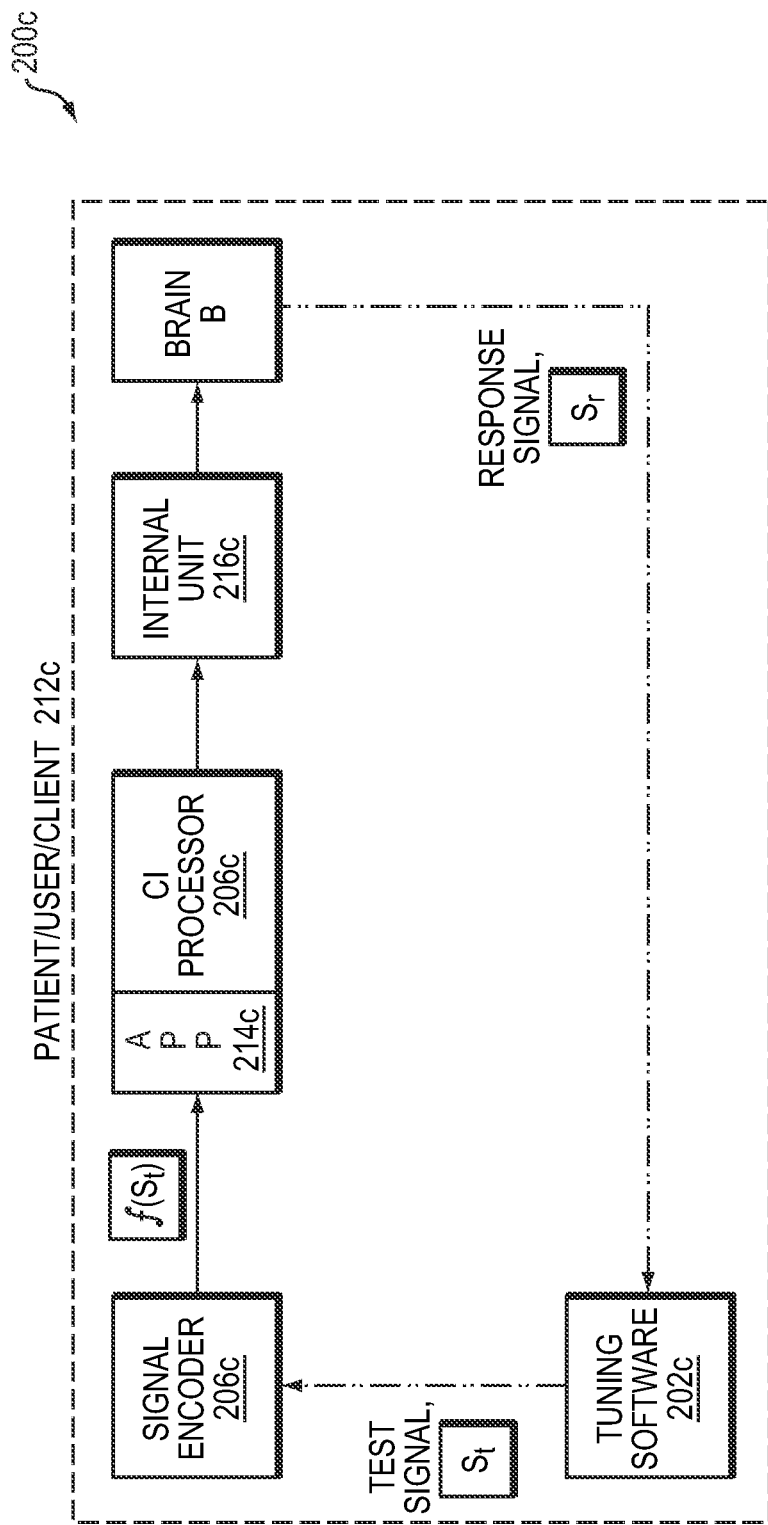

| PARAMETER | DEFAULT | OPTIONS |
|---|---|---|
| STRATEGY | ACE | ACE, CIS, SPEAK |
| STIMULATION RATE | 750 Hz | 250 - 2400 Hz |
| PULSE WIDTH | 25μs | 25 - 400μs |
| NUMBER OF CHANNELS | 20 | < 22 |
| NUMBER OF MAXIMA | 8 | < 12 |
| FREQUENCY ALLOCATION | LOG-LINEAR FROM 250 - 10000 Hz | MULTIPLE OPTIONS |
| GAIN | FLAT | MULTIPLE OPTIONS |
| GLOBAL THRESHOLD AND COMFORT MODIFIERS | NONE | INCREMENTS OF 1 - 30% |
| Q-VALUE | 20 | < 30 |
| BASE LEVEL | 4 | 0-6 |
| JITTER | 0% | 20% |

| CI MAPPING STRATEGY PARAMETERS |
|---|
| In general the following principals apply for the CI Device Speech Processing strategies:<br>• Spectral resolution (SPEAK)<br>   ° Site of stimulation: channel selection<br>   ° Large number of channels desirable<br>• Temporal resolution (CIS)<br>   ° Amplitude pattern of stimulation at a site<br>   ° High pulse rate on each channel desirable<br>• The ACE strategy is a combination of both spectral and temporal resolution<br><br>Parameters that must be chosen prior to measurements of Thresholds and Comfort Values:<br>  1. Stimulation Rate***<br>     a. For CIS: rate X number of Channels < 14,400 Hz<br>     b. For ACE and SPEAK: Rate X number of Maxima < 14,400 Hz<br>  2. Pulse width (Default is 25µs; range is from 25 - 150µs)<br>  *** for higher stimulation rates the Ts and Cs measured can be used for either an ACE<br>     or CIS map as long as the total stimulation rate does not exceed 14,400 Hz<br><br>Parameters that can be changed once the Threshold and Comfort Values have been obtained:<br>  1). Number of Channels (CIS) or number of maxima (SPEAK or ACE) as long as total<br>     stimulation rate does not exceed 14,400 Hz<br>  2). Deactivation of selected channels<br>  3). Frequency Allocation<br>  4). Gain - either globally or for individual channels<br>  5). Global T and C modifiers<br>  6). Q-Value - global modifier that changes the slope digital input level to the stimulus<br>     level output - amplitude curve<br>  7). Base Level - minimum input level that produces stimulation<br>     a. Decreasing: softer sounds are audible [increases the Input Dynamic Range<br>        (IDR) of the processor]<br>     b. Increasing: softer sounds are not processed<br>  8). Jitter: % of random variation to pulse rate<br>  9). Channel ordering - in very rare cases the cochlea does not follow the normal<br>     tonotopic organization of the normal auditory system |

FIG. 5B

SYSTEMS AND METHODS FOR REMOTELY TUNING HEARING DEVICES

CROSS-REFERENCE TO RELATED APPLICATIONS

This application is a continuation-in-part of U.S. patent application Ser. No. 11/421,889, filed Jun. 2, 2006, entitled "Speech-Based Optimization of Digital Hearing Devices"; which is a continuation-in-part of U.S. patent application Ser. No. 10/872,313, filed Jun. 18, 2004, now U.S. Pat. No. 7,206,416, entitled "Speech-Based Optimization of Digital Hearing Devices"; which claims the benefit of U.S. Provisional Patent Application Ser. No. 60/492,103, filed Aug. 1, 2003, the disclosures of which are hereby incorporated by reference herein in their entireties. Additionally, this application claims the benefit of U.S. Provisional Patent Application No. 61/164,450, filed Mar. 29, 2009, the disclosure of which is hereby incorporated by reference herein in its entirety.

FIELD OF THE INVENTION

This invention relates generally to systems and methods for tuning perceptual devices, and more specifically, to systems and methods for tuning perceptual devices, such as cochlear implants, at a location remote from the perceptual devices.

BACKGROUND

Hearing impaired persons may be fitted with a perceptual device, such as a digital hearing aid, a cochlear implant, etc., to improve or otherwise augment their hearing ability. Alternatively, the user of such a device may be fitted with only a part of a device. The device should be tuned to each user's perceptual capabilities such that each user can get the maximum benefit from his or her device. To tune the device, an agent, such as an audiologist or tuning software, such as that disclosed in U.S. Pat. No. 7,206,416, tests the user's perceptual ability with appropriate perceptual signals and suggests device parameter values based at least in part on the user's performance in the tests.

One example of a perceptual device is a multi-channel cochlear implant (CI) system. These CI systems include of an external headset with a microphone and transmitter, a body-worn or ear-level speech processor with a battery supply, and an internal receiver and electrode array. The microphone detects sound information and sends it to the speech processor which encodes the sound information into a digital signal. This information then is sent to the headset so that the transmitter can send the electrical signal through the skin via radio frequency waves to the internal receiver located in the mastoid bone of an implant recipient.

The receiver sends the electrical impulses to the electrodes implanted in the cochlea, thus stimulating the auditory nerve such that the listener receives sound sensations. Multi-channel CI systems utilize a plurality of sensors or electrodes. Each sensor is associated with a corresponding channel which carries signals of a particular frequency range. Accordingly, the sensitivity or amount of gain perceived by a recipient can be altered for each channel independently of the others.

In recent years, CI systems have made significant strides in improving the quality of life for profoundly hard of hearing individuals. CI systems have progressed from providing a minimal level of tonal response to allowing individuals having the implant to recognize upwards of 80 percent of words in test situations. Much of this improvement has been based upon improvements in speech coding techniques. For example, the introduction of Advanced Combination Encoders (ACE), Continuous Interleaved Sampling (CIS) and HiResolution, have contributed to improved performance for CI systems, as well as other digital hearing enhancement systems which incorporate multi-channel and/or speech processing techniques.

Once a CI system is implanted in a user, or another type of digital hearing enhancement mechanism is worn by a user, a suitable speech coding strategy and mapping strategy must be selected to enhance the performance of the CI system for day-to-day operation. Mapping strategy refers to the adjustment of parameters corresponding to one or more independent channels of a multi-channel CI system or other hearing enhancement system. Selection of each of these strategies typically occurs over an introductory period of approximately six or seven weeks during which the hearing enhancement system is tuned. During this tuning period, users of such systems are asked to provide feedback on how they feel the device is performing. The tuning process, however, is not a user-specific process. Rather, the tuning process is geared to the average user.

More particularly, to create a mapping for a speech processor, an audiologist first determines the electrical dynamic range for each electrode or sensor used. The programming system delivers an electrical current through the CI system to each electrode in order to obtain the electrical threshold (T-level) and comfort or max level (C-level) measures defined by the device manufacturers. T-level, or minimum stimulation level, is the softest electrical current capable of producing an auditory sensation in the user 100 percent of the time. The C-level is the loudest level of signal to which a user can listen comfortably for a long period of time.

The speech processor then is programmed, or "mapped," using one of several encoding strategies so that the electrical current delivered to the implant will be within this measured dynamic range, between the T- and C-levels. After T- and C-levels are established and the mapping is created, the microphone is activated so that the patient is able to hear speech and sounds in the environment. From that point on, the tuning process continues as a traditional hearing test. Hearing enhancement device users are asked to listen to tones of differing frequencies and volumes. The gain of each channel further can be altered within the established threshold ranges such that the patient is able to hear various tones of differing volumes and frequencies reasonably well. Accordingly, current tuning practice focuses on allowing a user to become acclimated to the signal generated by the hearing device.

The above-mentioned tuning technique has been developed to meet the needs of the average user. This approach has gained favor because the amount of time and the number of potential variables involved in designing optimal maps for individual users would be too daunting a task. For example, additional complications to the tuning process exist when users attempt to add subjective input to the tuning of the hearing enhancement system. Using subjective input from a user can add greater complexity to the tuning process as each change in the mapping of a hearing enhancement system requires the user to adjust to a new signal. Accordingly, after a mapping change, users may believe that their ability to hear has been enhanced, while in actuality, the users have not adjusted to the new mapping. As users adjust to new mappings, the users' hearing may in fact have been degraded.

In general, the equipment described generally above is extremely costly to purchase and is generally unavailable to a typical patient/user/client. Additionally, the user would need to know how to connect the various equipment components in order for that equipment to function satisfactorily. Many users, however, do not possess the technical knowledge to set up and operate this equipment. Since perceptual devices need only be tuned on an infrequent basis, the cost of obtaining the required equipment may be excessive. Accordingly, the equipment may be located at a facility that serves a number of users, such as the office of a doctor, audiologist, or other clinician. However, travel to these facilities for testing may be inconvenient or impossible.

What is needed, then, is a system that simplifies the tuning process for a user and reduces investment in tuning equipment, such that any perceptual device user may access and use the system. The system should utilize techniques for tuning hearing enhancement systems, including both CI systems and digital hearing aids, that bypass user subjectivity. These techniques should still allow hearing enhancement systems to be tuned on an individual basis. Further, such a technique should be time efficient.

SUMMARY OF THE INVENTION

The present invention, according to one embodiment, provides a solution for tuning hearing enhancement systems. The inventive arrangements disclosed herein can be used with a variety of digital hearing enhancement systems including, digital hearing aids and cochlear implant systems. Other exemplary systems in which the inventive arrangements disclosed herein can be used include mobile phones configured to communicate via a cellular communications network and/or wireless ad hoc network. Still another exemplary system is a telephone configured to communication via a Voice-over-Internet-Protocol (VoIP) network and/or adapted to communicate via a plain old telephone service (POTS) network. These various systems are herein referred to collectively as "hearing devices." In accordance with the present invention, rather than using conventional hearing tests where only tones are used for purposes of testing a hearing device, speech perceptual tests can be used.

More particularly, speech perceptual tests wherein various words and/or syllables of the test are representative of distinctive language and/or speech features can be correlated with adjustable parameters of a hearing device. By detecting words and/or syllables that are misrecognized by a user, the hearing device can be tuned to achieve improved performance over conventional methods of tuning hearing devices.

In other embodiments, the present invention provides a solution for characterizing various communications channels and adjusting those channels to overcome distortions and/or other deficiencies.

One aspect of the present invention can include a method of tuning a digital hearing device. The method can include playing portions of test audio, wherein each portion of test audio represents one or more distinctive features of speech, receiving user responses to played portions of test audio heard through the digital hearing device, and comparing the user responses with the portions of test audio. An operational parameter of the digital hearing device can be adjusted according to the comparing step, wherein the operational parameter is associated with one or more of the distinctive features of speech.

In another embodiment, the method can include, prior to the adjusting step, associating one or more of the distinctive features of the portions of test audio with the operational parameter of the digital hearing device. Each distinctive feature of speech can be associated with at least one frequency or temporal characteristic. Accordingly, the operational parameter can control processing of frequency and/or temporal characteristics associated with at least one of the distinctive features.

The method further can include determining that at least a portion of the digital hearing device is located in a sub-optimal location according to the comparing step. The steps described herein also can be performed for at least one different language as well as for a plurality of different users of similar hearing devices.

Another aspect of the present invention can include a method of evaluating a communication channel. The method can include playing, over the communication channel, portions of test audio, wherein each portion of test audio represents one or more distinctive features of speech. The method can include receiving user responses to played portions of test audio, comparing the user responses with the portions of test audio, and associating distinctive features of the portions of test audio with operational parameters of the communication channel.

In another embodiment, the method can include adjusting at least one of the operational parameters of the communication channel according to the comparing and associating steps. Notably, the communication channel can include an acoustic environment formed by an architectural structure, an underwater acoustic environment, or the communication channel can mimic aviation effects on speech and hearing. For example, the communication channel can mimic effects such as G-force, masks, and the Lombard effect on hearing. The steps disclosed herein also can be performed in cases where the user exhibits signs of stress or fatigue.

Other embodiments of the present invention can include a machine readable storage programmed to cause a machine to perform the steps disclosed herein as well as a system having means for performing the various steps described herein.

In one aspect, the invention relates to a system for tuning a hearing device, the system including a first transmitter for sending a test signal to a model of a hearing device, an encoder for encoding the test signal, a processor for setting a parameter of the model, wherein the parameter is based at least in part on the measured response, a second transmitter for sending the encoded test signal to a hearing device associated with a user, a receiver for receiving a user response, wherein the user response is based at least in part on the encoded signal, and a comparison module for comparing the user response to the test signal. In an embodiment, the system includes a test set generator for generating a test signal. In another embodiment, the test set generator and the comparison module are located remote from the hearing device. In yet another embodiment, the signal encoder and the model of the hearing device are located remote from the hearing device. In still another embodiment, the system includes an adjustment module for selecting an operational parameter of the hearing device based at least in part on a comparison of the user response and the test signal.

In another embodiment of the above aspect, the second transmitter transmits the operational parameter to the hearing device. In another embodiment, the encoded test signal has at least one distinctive feature of speech. In yet another embodiment, the at least one distinctive feature of speech is at least one of a fundamental source feature, a secondary consonantal source feature, and a resonance feature. In still another embodiment, the system includes an association module for associating the operational parameter of the hearing device with the at least one distinctive feature of speech. In another embodiment, the encoded test signal is sent over a network. In another aspect, the invention relates to a digital hearing device including the above-recited system.

In another aspect, the invention relates to a method of tuning a hearing device, the method including the steps of sending a test signal to a model of a hearing device, encoding the test signal, sending the encoded test signal to a hearing device associated with a user, receiving a user response based at least in part on the encoded test signal, comparing the user response with the test signal, and sending at least one operational parameter to the hearing device based at least in part on the comparison. In an embodiment, the method includes the step of selecting a test signal. In another embodiment, the test signal includes at least one feature of speech. In yet another embodiment, the encoding step includes digitizing the at least one feature of speech. In still another embodiment, the encoding step includes adjusting a characteristic of the feature of speech.

In another embodiment of the above aspect, the characteristic of the feature of speech includes at least one of a fundamental source feature, a secondary consonantal source feature, and a resonance feature. In another embodiment, the test signal includes an electrical signal corresponding to a stimuli comprising at least one feature of speech. In another embodiment, the method includes the step of associating the operational parameter of the hearing device with the at least one feature of speech. In yet another embodiment, the encoded test signal is sent over a network. In still another embodiment, the network is TCP/IP enabled.

In another embodiment of the above aspect, the model of the hearing device is located remote from the hearing device. In another embodiment, the model of the hearing device is collocated with the hearing device. In yet another embodiment, the method includes the step of receiving at the hearing device the encoded test signal and processing the encoded test signal. In still another embodiment, the processing step includes reproducing the at least one feature of speech.

In another aspect, the invention relates to an article of manufacture having computer-readable program portions embedded thereon for tuning a hearing device, the program portions including instructions for sending a test signal to a model of a hearing device, instructions for encoding the test signal, instructions for sending the encoded test signal to a hearing device associated with a user, instructions for receiving a user response based at least in part on the encoded test signal, instructions for comparing the user response with the test signal, and instructions for sending at least one operational parameter to the hearing device based at least in part on the comparison.

BRIEF DESCRIPTION OF THE DRAWINGS

There are shown in the drawings, embodiments which are presently preferred, it being understood, however, that the invention is not limited to the precise arrangements and instrumentalities shown.

FIG. 2C is a schematic diagram of a system for tuning a perceptual device using a local server and local external device components in accordance with another embodiment of the invention.

FIGS. 5A and 5B are tables illustrating exemplary operational parameters of one variety of hearing enhancement system, such as a Cochlear Implant, that can be modified using suitable control software.

DETAILED DESCRIPTION OF THE INVENTION

Figure 1:
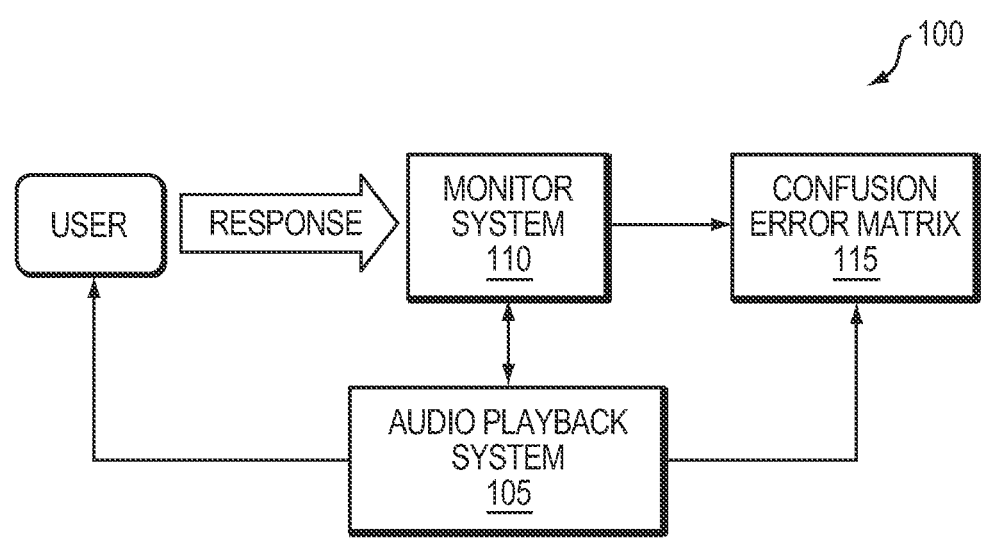
FIG. 1 is a schematic diagram illustrating an exemplary system for determining relationships between distinctive features of speech and adjustable parameters of a hearing enhancement system in accordance with the inventive arrangements disclosed herein.

FIG. 1 is a schematic diagram illustrating an exemplary system 100 for determining relationships between distinctive speech and/or language features and adjustable parameters of a hearing enhancement system (hearing device) in accordance with the inventive arrangements disclosed herein. As previously noted, such hearing devices can include any of a variety of digital hearing enhancement systems such as cochlear implant systems, digital hearing aids, or any other such device having digital processing and/or speech processing capabilities. Other hearing devices, in accordance with the invention, can include voice-based communication systems such as mobile phones configured to communicate via a cellular communications network and/or wireless ad hoc network, as well as telephones configured to communication via a Voice-over-Internet-Protocol (VoIP) network and/or adapted to communicate via a plain old telephone service (POTS) network. Additionally, speakers or headphones are also contemplated.

More particularly, the system 100 can include an audio playback system (playback system) 105, a monitor 110, and a confusion error matrix (CEM) 115. The playback system 105 can audibly play recorded words and/or syllables to a user having a hearing device to be tuned. The playback system 105 can be any of a variety of analog and/or digital sound playback systems. According to one embodiment of the present invention, the playback system 105 can be a computer system having digitized audio stored therein. According to still another embodiment, the playback system 105 can include a text-to-speech (TTS) system capable of generating synthetic speech from input or stored text.

While the playback system 105 can simply play aloud to a user recorded and/or generated audio, it should be appreciated that in some cases the playback system 105 can be communicatively linked with the hearing device under test. For example, in the case of selected digital hearing aids and/or cochlear implant systems, an A/C input jack can be included in the hearing device that allows the playback system 105 to be connected to the hearing device to play audio directly through the A/C input jack without having to generate sound via acoustic transducers.

The playback system 105 can be configured to play any of a variety of different test words and/or syllables to the user (test audio). Accordingly, the playback system 105 can include or play commonly accepted test audio. For example, according to one embodiment of the present invention, the well-known Iowa Test Battery, as disclosed by Tyler et al. (1986), of consonant vowel, consonant nonsense words can be used. As noted, depending upon the playback system 105, a media such as a tape or compact disc can be played, the test battery can be loaded into a computer system for playback, or the playback system 105 can generate synthetic speech mimicking a test battery.

Regardless of the particular set or listing of words and/or syllables used, each of the words and/or syllables can represent a particular set of one or more distinctive features of speech. Two distinctive feature sets have been proposed. The first set of features, proposed by Chompsky and Halle (1968), is based upon the articulatory positions underlying the production of speech sounds.

Another set of features, proposed by Jakobson, Fant, and Halle (1963), is based upon the acoustic properties of various speech sounds. These properties describe a small set of contrastive acoustic properties that are perceptually relevant for the discrimination of pairs of speech sounds. More particularly, as will be readily understood by one of ordinary skill, the different distinctive features and their potential acoustic correlates can be broadly grouped into three categories: fundamental source features; secondary consonantal source features; and resonance features.

The fundamental source features can be further characterized on the basis of whether the speech sounds are vocalic or non-vocalic. Vocalic speech corresponds to speech sounds associated with vowels. Accordingly, such speech sounds correspond to a single periodic source, the onset of the speech not being abrupt; otherwise the speech sound can be characterized as non-vocalic. The fundamental source features also can be characterized on the basis of whether the speech sounds are consonantal or non-consonantal. Consonantal speech sounds correspond to sounds associated with consonants. Such speech sounds are characterized by the presence of zeros in the associated spectrum of the sounds.

The secondary consonantal source features can be further characterized on the basis of whether the speech sounds are interrupted or continuant. Continuant speech sounds, are also characterized as semi-vowels, because of their similar sound quality. There is little or no friction with continuant speech sounds as the air passes freely out through the mouth of the speaker. A continuant speech sound is produced with an incomplete closure of the vocal tract. Interrupted speech sounds, by contrast, end abruptly.

The secondary consonantal features can also be characterized on the basis of whether the speech sounds are checked or unchecked. Checked speech sounds, typified by some Far Eastern and African languages, are characterized by abrupt termination as opposed to gradual decay, whereas unchecked speech sounds are characterized by gradual decay. Additionally, secondary consonantal features can be characterized as strident or mellow. The former typically has an irregular waveform, whereas the latter typically has a smooth waveform. A secondary consonantal feature characterize as mellow also has a wider autocorrelation function relative to a corresponding normalized strident feature. Secondary consonantal features can also be classified according to whether the sound is voiced or voiceless.

The resonance features can be further characterized on the basis of whether the speech sound is compact or diffuse. A compact feature is associated with sound having a relative predominance of one centrally located format region, whereas a diffuse features implies sound having one or more non-central formats. The resonance features can also be characterized as grave or acute. Speech sounds that are characterized as grave are low-frequency dominant low frequency, whereas those characterized as acute are high-frequency dominant. Additionally, resonance features can be characterized as flat or plain, depending on whether the there is a downward shift of some or all formats, typically associated with vowels and a reduction in lip orifice of the speaker.

The resonance features also can be further characterized as sharp or plain, the latter characterizing speech sounds whose second and/or higher formats rise. Moreover, resonance features can also be characterized as tense or lax, depending on the amount and duration of the energy of the sound. The resonance features also can be classified according to whether the speech sound is characterized as having a nasal format or a nasal murmur. The distinctive speech features and their potential acoustic correlates are further described in R. Jakobson, G. M. Fant, and M. Halle, PRELIMINARIES TO SPEECH ANALYSIS: THE DISTINCTIVE FEATURES AND THEIR CORRELATES (MIT Press, Cambridge; 1963), which is incorporated herein by reference in its entirety.

The above-described distinctive features of speech sounds and their potential acoustic correlates are only examples of the many different distinctive features of speech for which a relationship with one or more adjustable parameters can be determined according to the invention described herein. Accordingly, regardless of the particular distinctive features of speech of interest in a particular context the invention can determine relationships between the distinctive features and adjustable parameters for enhancing the capacity of a particular hearing device for a particular user of the device.

It should be appreciated that any of a variety of different features of speech can be used within the context of the present invention. Any feature set that can be correlated to test words and/or syllables can be used. As such, the invention is not limited to the use of a particular set of speech features and further can utilize a conglomeration of one or more feature sets.

The monitor system 110 can be a human being who records the various test words/syllables provided to the user and the user responses. In another embodiment, the monitor system 110 can be a speech recognition system configured to speech recognize, or convert to text, user responses. For example, after hearing a word and/or syllable, the user can repeat the perceived test audio aloud.

In yet another embodiment, the monitor system 110 can include a visual interface through which the user can interact. The monitor system can include a display upon which different selections are shown. Thus, the playback of particular test words or syllables can be coordinated and/or synchronized with the display of possible answer selections that can be chosen by the user. For example, if the playback system 105 played the word "Sam," possible selections could include the correct choice "Sam" and one or more incorrect choices, such as "sham." The user chooses the selection corresponding to the user's understanding or ability to perceive the test audio.

In any case, the monitor system 110 can note the user response and store the result in the CEM 115. The CEM 115 is a log of which words and/or syllables were played to the user and the user responses. The CEM 115 can store both textual representations of test audio and user responses and/or the audio itself, for example as recorded through a computer system or other audio recording system. As shown, the audio playback system 105 can be communicatively linked to the CEM 115 so that audio data played to the user can be recorded within the CEM 115.

While the various components of system 100 have been depicted as being separate or distinct components, it should be appreciated that various components can be combined or implemented using one or more individual machines or systems. For example, if a computer system is utilized as the playback system 105, the same computer system also can store the CEM 115. Similarly, if a speech recognition system is used, the computer system can include suitable audio circuitry and execute the appropriate speech recognition software.

Depending upon whether the monitor system 115 is a human being or a machine, the system 100, for example the computer, can be configured to automatically populate the confusion error matrix 115 as the testing proceeds. In that case, the computer system further can coordinate the operation of the monitor system 110, the playback system 105, and access to the CEM 115. Alternatively, a human monitor 110 can enter testing information into the CEM 115 manually.

In order to reduce the cost associated with equipment purchase, or to reduce or eliminate the travel time required to reach a testing facility, the present invention contemplates a tuning system that may be used over a standard internet or network connection. In general, the equipment described generally above needed to run such tests on a user or client side includes: a computer, an internet connection (preferably high speed); a commercial-grade sound card; a high-quality microphone (preferably one that can pick up energy at least up to 8000 Hz); a TV/AV device cable; a USB cable/device programming pod; a custom programming boot; and an implant external processor and radio coupler.

In certain cases, most of the equipment described above may be located at a site, such as a remote application server, which may be accessed by any user as desired. By using a remote server, ease-of-use and cost reduction for the user may be improved. Moreover, since this site may serve multiple users substantially simultaneously, investment costs may be further reduced. Disclosed herein are several embodiments of the remote tuning system and method, depending on the location of the application server and its contents. In any embodiment, the tuning agent may be tuning software, such as that disclosed herein, although other tuning software may be utilized. Alternatively, the tuning agent may be a human audiologist. The data exchanged between the agent and the user may include perceptual signals (e.g., audio signals representing vowel-consonant-vowel phonemes, words, tones, etc.) and/or perceptual device parameter values (e.g., the stimulation rate of a cochlear implant (CI) device may be set to about 900 Hz—other values are also contemplated). It is advantageous to transmit this information to the user in real time without any loss or distortion. Faulty information may have the negative consequence of reducing or damaging the user's perceptual ability, or may cause the device to be improperly tuned.

Figure 2A:
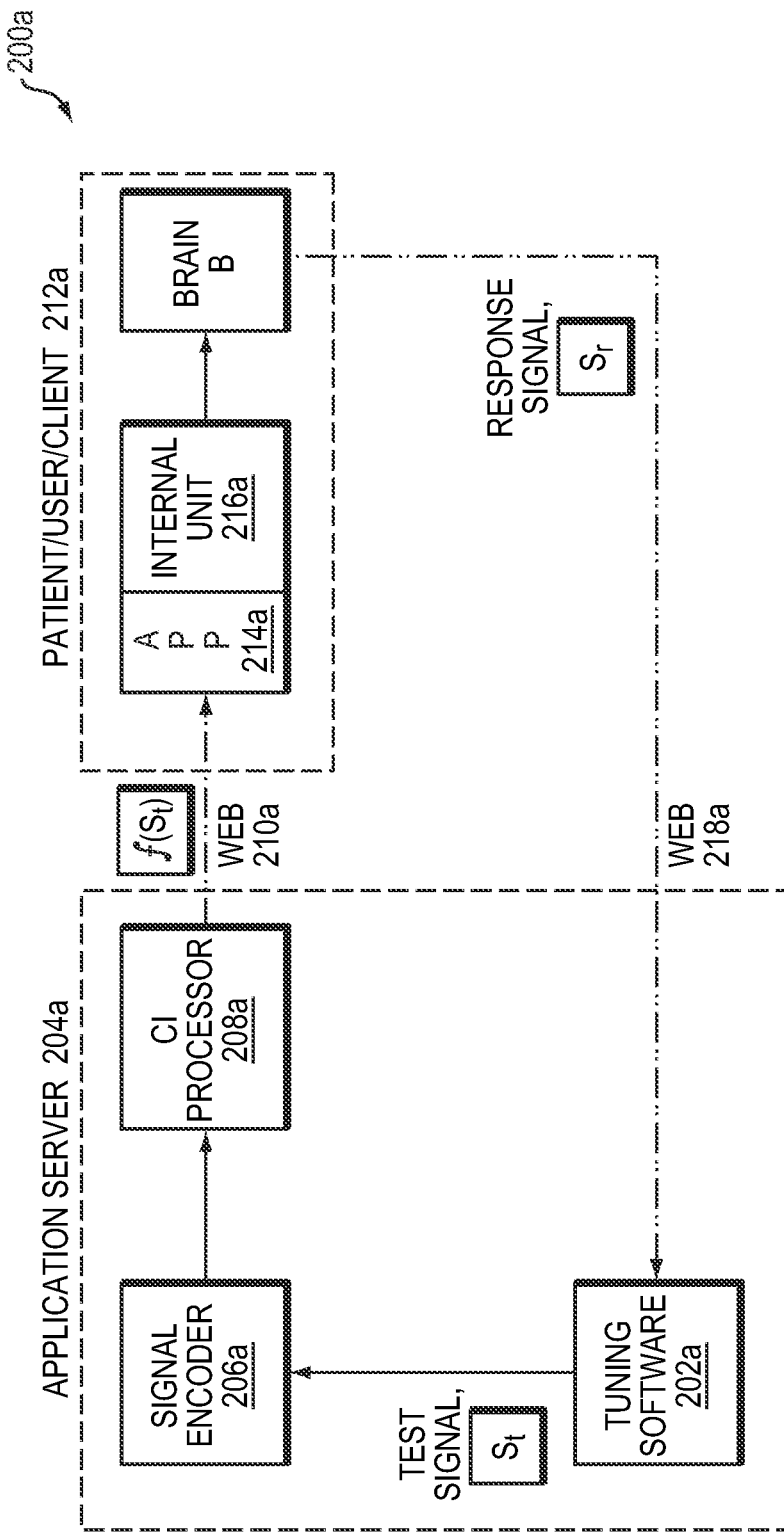
FIG. 2A is a schematic diagram of a system for tuning a perceptual device using a remote server and remote external device components in accordance with one embodiment of the invention.

FIG. 2A depicts one embodiment of the tuning system 200a, which allows a user to remotely access the monitor system 105, monitor system 110, and confusion error matrix 115 (depicted in FIG. 1), even if that equipment is located remotely from the user. As depicted in FIG. 2A, the agent (in this case, tuning software 202a), is located in an application server 204a along with external parts of a CI device, such as a signal encoder 206a and a CI processor 208a. In certain embodiments, the signal encoder and CI processor may be contained within a single module. The signal encoder 206a and a CI processor 208a are one or more models of the hearing device being tuned. These models may be obtained, for example, from Cochlear Limited, MED-EL Corporation, Advanced Bionics Corporation, Sonova Holding AG, Oticon A/S, and Widex A/S. The tuning software 202a sends a test signal $S_t$ to the signal encoder 206a that in conjunction with the CI processor 208a, encodes the signal. The methods of encoding are described below with regard to FIG. 2D. The application server 204a sends the encoded test signal $f(S_t)$ via an internet 210a or other network connection to the user side 212a of the system 200a. The internet or network connection may be a Bluetooth or other wireless connection.

The application (or APP) 214a running in a personal computer (PC) on the user side 212a, deciphers the encoded test signal $f(S_t)$ received via the web 210a. It may also determine whether the received signal and/or suggested device parameters are detrimental to the user (e.g., if the signal volume is too high). The internal unit 216a of the CI is directly connected to the user's PC. In alternative embodiments, the internal unit may be directly connected to the network. The internal unit 216a sends an intermediate signal to the user's brain B. The intermediate signal emanated from the device and perceived by the user (i.e., it is the stimulus actually heard by the user). The user response may be in the form of a response signal $S_r$. The response signal $S_r$ may be a sound repeated by the user into a PC microphone, or the user may type a textual representation of the sound heard into a PC keyboard. Other types of response signals are contemplated. For example, the user may select from two or more possible choices presented on a PC monitor. The response signal $S_r$ is sent via a web 218a or other network connection to the tuning software 202a, which then suggests another test signal $S_t$, terminates the tuning session, or takes other action. Additionally, the tuning software compares the response signal $S_r$ to the test signal $S_t$ and may suggest adjustment to the hearing device parameters to improve user perceptual ability. The tuning software may also associate operational parameters of the hearing device with distinctive features of speech that were components of the initial test signal $S_t$.

In another embodiment of the system depicted in FIG. 2A, the internal unit may be headphones or speakers or a combination thereof. The test described may include testing the user wearing the headphones, and using the user responses to set the parameters of a hearing device model. This model may, in turn, be used to optimize an actual hearing device that is later sent to the user subsequent to testing.

Figure 2B:
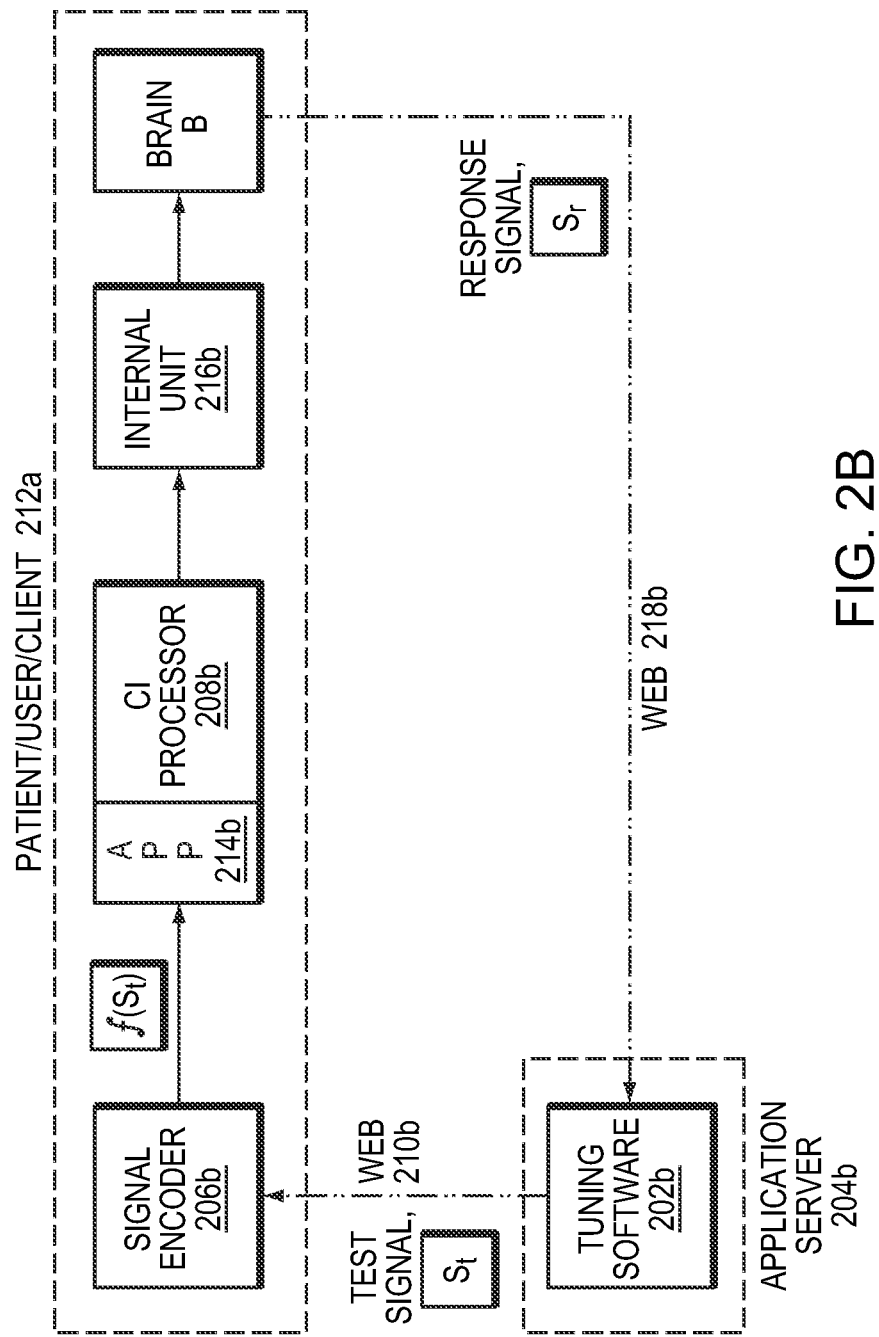
FIG. 2B is a schematic diagram of a system for tuning a perceptual device using a remote server and local external device components in accordance with another embodiment of the invention.

FIG. 2B depicts another embodiment of the testing system 200$b$, wherein only tuning software 202$b$ is located remotely on an application server 204$b$. In this embodiment, a signal encoder 206$b$ and a CI processor 208$b$ reside with on a user side 212$b$ of the system 200$b$. These external parts of the CI device may be directly connected to the user's PC. An application 214$b$, running in the user's PC, deciphers the information received via an internet or other connection 210$b$. In the depicted embodiment, the application 214$b$ may be integral with the signal encoder 206$b$, and may, in conjunction with the signal encoder 206$b$, encode the test signal $S_t$, prior to sending the encoded test signal $f(S_t)$ to the CI processor 208$b$. Information sent via the web 210$b$ may include the test signal $S_t$ or instruction about which audio files to play based on the user's responses, if digital sound files have been installed on the PC along with the application 214$b$. Again, the application 214$b$ may determine whether the received signal and/or suggested device parameters are detrimental to the user. Alternatively or additionally, the manufacturer's software located within in the device may make such a determination. Information is then set to the internal unit, which then sends an intermediate signal to the user's brain B. A response signal $S_r$ is sent via a web 218$b$ or other network connection to the tuning software 202$b$.

FIG. 2C depicts another embodiment of the testing system 200$c$, wherein the device may be self-tuned without the need for any application server or the web. In this embodiment, the tuning software 202$c$ is installed in the device, which may obviate the need for a user PC. The user's responses are received by a microphone located within the device itself. Additional memory, processor speed, etc., in the device may be beneficial to record and store the user's responses and to suggest subsequent test signals and device parameters. The components, signals, etc. incorporated into the system 200$c$ are described above with regard to the embodiments of FIGS. 2A and 2B. In certain embodiments where the device is self-tuned without the need for the application server, the signal encoder may be eliminated, such that $S_t$ is identical to $f(S_t)$.

Figure 2D:
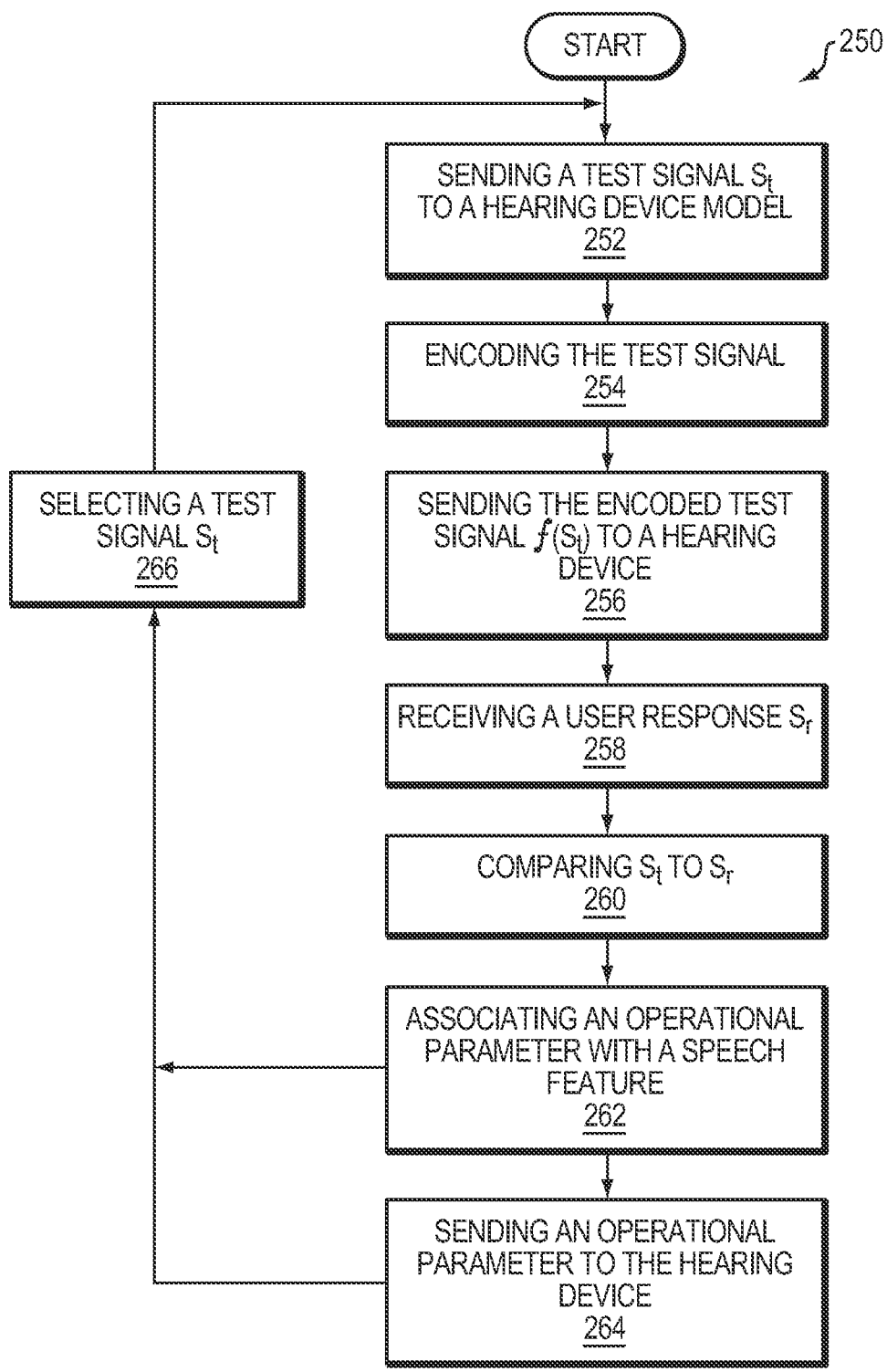
FIG. 2D is a flow chart illustrating a method of tuning a perceptual device using a local server and local external device components in accordance with another embodiment of the invention.

FIG. 2D depicts a method of tuning a perceptual device 250 in accordance with the embodiments of FIGS. 2A-2C. First, a test signal $S_t$ is sent to a model of a hearing device (Step 252). This test signal is then encoded by the model (Step 254). Different methods of encoding the test signal are contemplated. For example, if the test signal $S_t$ is an audible signal, the test signal $S_t$ may be digitized to ensure accurate transmission of the signal (ensuring the hearing device user is tested with an accurate representation or reproduction of the audible sound. In another embodiment, the on or more characteristics of the audible signal (that is, one or more characteristic features of speech) may be adjusted. These features of speech may include a fundamental source feature, a secondary consonantal source feature, and a resonance feature. Other characteristics of the audible signal (for example, volume, pitch, rate, vowel identity, speaker identity, etc.) may be adjusted as desired for a particular application. Other embodiments of the tuning system may encode a test signal $S_t$ that is an electrical signal corresponding to a stimuli including a feature of speech.

Encoding of the test signal St by use of a model of the hearing device helps ensure the desired stimuli is recreated for the user in a controlled and consistent form. Encoding controls the hearing instrument and the presentation of the test signal St. Controlling the hearing device is desirable since the device has the potential to alter the test signal. It is also desirable to ensure that the device parameters are in the desired settings for the current test stimuli. The test signal St presentation (dB level) to the hearing device should be controlled as well, since a consistent test signal presented to the user is desirable to ensure accurate results.

Control of the test signal presentation level means, in one embodiment, understanding the distance the user is from the signal, as well as understanding the system that presents the sounds to the user. Since controlling the equipment being used to present the signal (computer, operating system, sound cards, speakers, network connection, etc.) at the remote location can be very difficult, encoding the signal helps to remove as many unknowns as possible from the tuning process. A model of the hearing device can be used to create a signal that can be recreated at the remote location in a consistent form. For example, the CI model can be used to transform the test stimuli into an electrical impulse that can be encoded and sent to the user over the web and delivered to the user at the desired level with a known state of the CI (i.e., the parameter settings). In the above example, the modeling of the CI would have removed the need to present an audio signal on the receive side while ensuring a known signal was sent to the user. Encoding the signal is focused on removing as many unknown on the receive side as possible to unsure a controlled signal is delivered to the user.

This encoded test signal $f(S_t)$ is then sent to a perceptual device, which may be a CI device or other hearing device (Step 256). At this point, the application described above may decode or otherwise process the encoded test signal $f(S_t)$ and deliver it to the user, via the internal CI unit. Next, a user response $S_r$, is received (Step 258). The user response $S_r$ is at least partially defined by the encoded test signal $f(S_t)$, and indicates what the user heard as a result of the encoded test signal $f(S_t)$. The test signal $S_t$ and user response $S_r$ are then compared, usually by tuning software (Step 260). As described above, the tuning software may be remote from or integral with other components of the testing system. Next, the operational parameters may be associated with a feature of speech (Step 262) which, in certain embodiments, may be a distinctive feature of speech. The results of the comparison are used to tune the CI device. For example, the operational parameters of the CI device may be adjusted or tuned (Step 264), in accordance with the techniques described herein. The tuning software sends adjustments to the hearing device, either in conjunction with another test signal or separately therefrom. These adjustments help improve the quality of perception by the device user. If testing continues, a new test signal $S_t$ may be selected (Step 266). As depicted in FIG. 2D, after Step 262, another test signal may immediately be selected, encoded, and sent. This loop may be repeated until Step 264 is performed at the end of the testing routine. Alternatively, Step 264 may be performed at the end of each comparison. In another embodiment, the testing may begin with one or more operational parameters being sent to the hearing device, to initially set the baseline device settings.

Figure 3A:
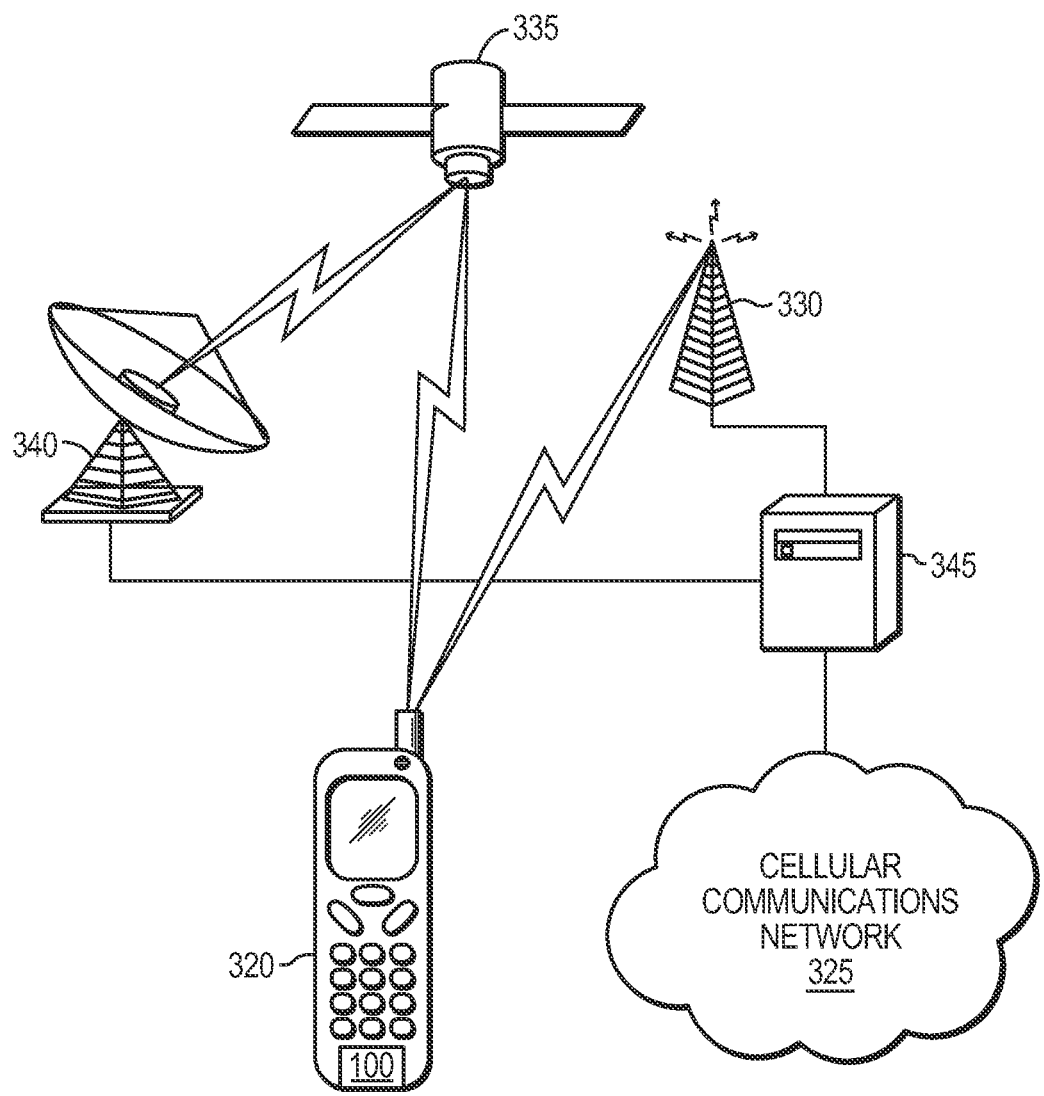
FIG. 3A is a schematic diagram of a cellular phone configured to communicate via a cellular communications network and including a system for determining relationships between distinctive features of speech and adjustable parameters in order to tune the cellular phone to the hearing requirements of a particular user in accordance with the inventive arrangements disclosed herein.

FIG. 3A is a schematic diagram of a communications environment in which the system 100, as described can be employed according one embodiment of the invention. The communications environment is a cellular communication environment in which the particular hearing device is cellular phone 320. The system 100 is illustratively integrated into the cellular phone 320. The cellular phone 320 can communicate via cellular communications network 325 with other communications devices (not shown) that also communicatively link to the cellular communications network. The cellular phone 320 illustratively conveys and receives wireless communications signals via a cellular tower 330 and/or a communications satellite 335, the latter also illustratively communicating via wireless signals to a ground station 340. Signals between the cellular tower 330 and ground station 340 are illustratively exchanged with a server 345 or other application-specific device, as will be readily understood by one of ordinary skill in the art.

In performing the functions described herein, the system 100 can be used to improve or optimize the cellular phone 320 so as to accommodate the unique hearing needs of a particular user of the device. Specifically, the system 100 allows the cellular phone to be programmed to present a series of speech sounds to a user of the cellular phone 320 in which the system is integrated. The user can repeat the sounds into the cellular phone 320. The system-presented sounds and the user's response, are compared using automatic speech recognition techniques based upon distinctive feature analysis, according to the invention. The difference—or errors—obtained using two sets of distinctive features can be used to tune the cellular phone 320; that is, the comparison and distinctive feature analysis applied by the system, provides a basis by which to adjust operation parameters of the device to accommodate the particular hearing needs of the user. Appropriate tuning can improve the intelligibility of the speech heard by the user of the cellular phone 320.

Figure 3B:
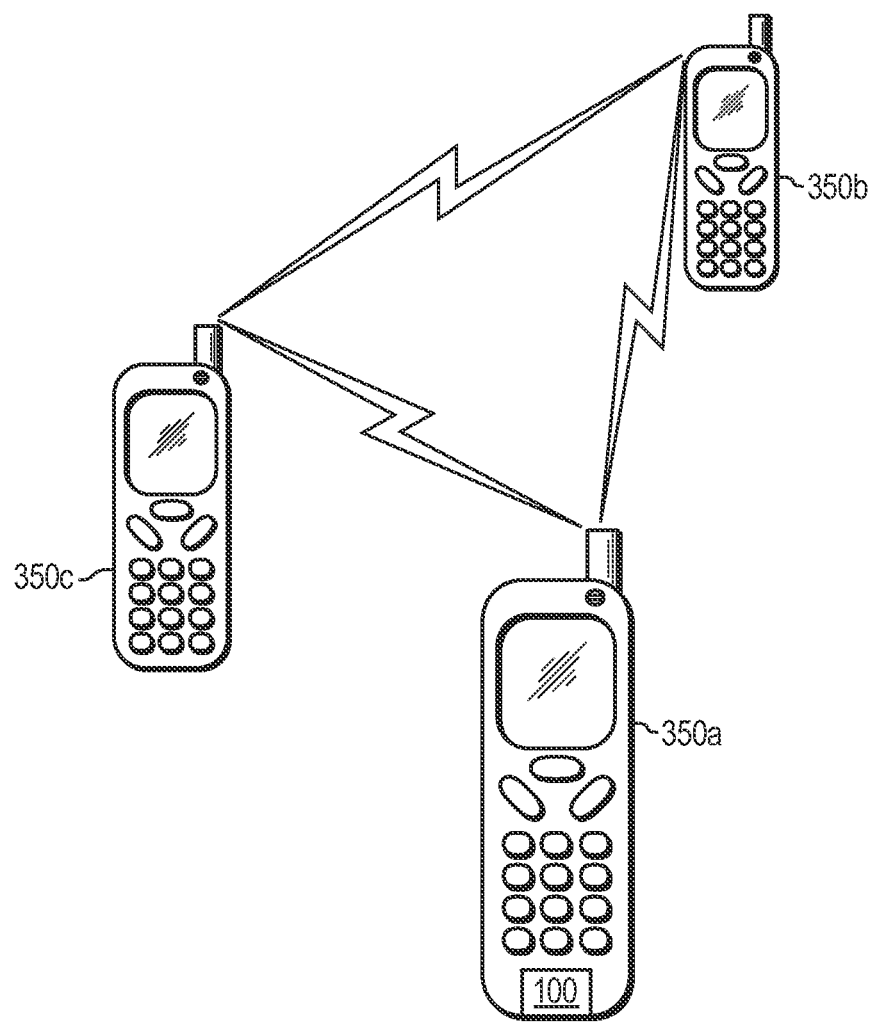
FIG. 3B is a schematic diagram of a mobile phone configured to communicate via a wireless ad hoc communications network and including a system for determining relationships between distinctive features of speech and adjustable parameters in order to tune the cellular phone to the hearing requirements of a particular user in accordance with the inventive arrangements disclosed herein.

FIG. 3B is a schematic diagram of an alternative communications environment in which the system 100, as described, can be employed according to yet another embodiment of the invention. The illustrated environment, according to this embodiment, comprises an ad hoc wireless network in which a plurality of wireless communications devices 350a-c communicate directly with one another through the exchange of wireless communications signals. At least one of the plurality of devices defines a hearing device 350a, which according to the present invention, includes the system 100 having the afore-described components of the system integrated into the device. Operatively, the system 100 presents sounds and compares the users response, comparing the differences and applying distinctive feature analysis, the system 100 tunes the mobile device 350a. Thus, again, the system 100 can be used to improve or optimize the mobile hearing device 350a so as to accommodate the specific hearing needs of the user.

Figure 3C:
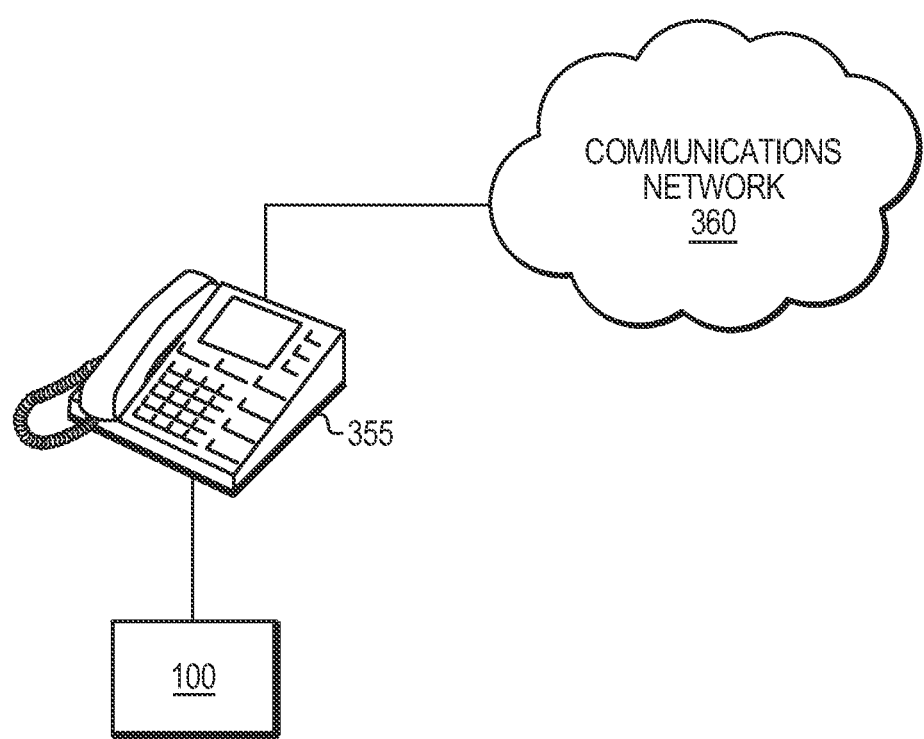
FIG. 3C is a schematic diagram of a telephone configured to communicate via a telephony communications network and including a system for determining relationships between distinctive features of speech and adjustable parameters in order to tune the telephone to the hearing requirements of a particular user in accordance with the inventive arrangements disclosed herein

FIG. 3C is a schematic diagram of yet a different communications environment in which the system 100 can be employed according to still another embodiment of the invention. Within this environment, the hearing device is a telephone 355, such as a plain old telephone service (POTS) telephone or a VoIP telephone, configured to communicate with other devices (not shown) via a communications network 360 which comprises a POTS and/or data communications network. The system 100, whose components and operative features are those described herein, illustratively comprises a separate unit communicatively linked to the telephone 355. Alternatively, however, the system can be integrated into the telephone 355. Operatively, the system 100 presents to the user of the telephone 355 certain sounds. Differences—or errors—between the device-presented sounds and the user's response to the sounds are compared. Applying distinctive feature analysis, as described herein, the system 100 tunes the telephone 355 so that the telephone is operatively configured to accommodate the particular hearing needs of the telephone user.

Figure 4:
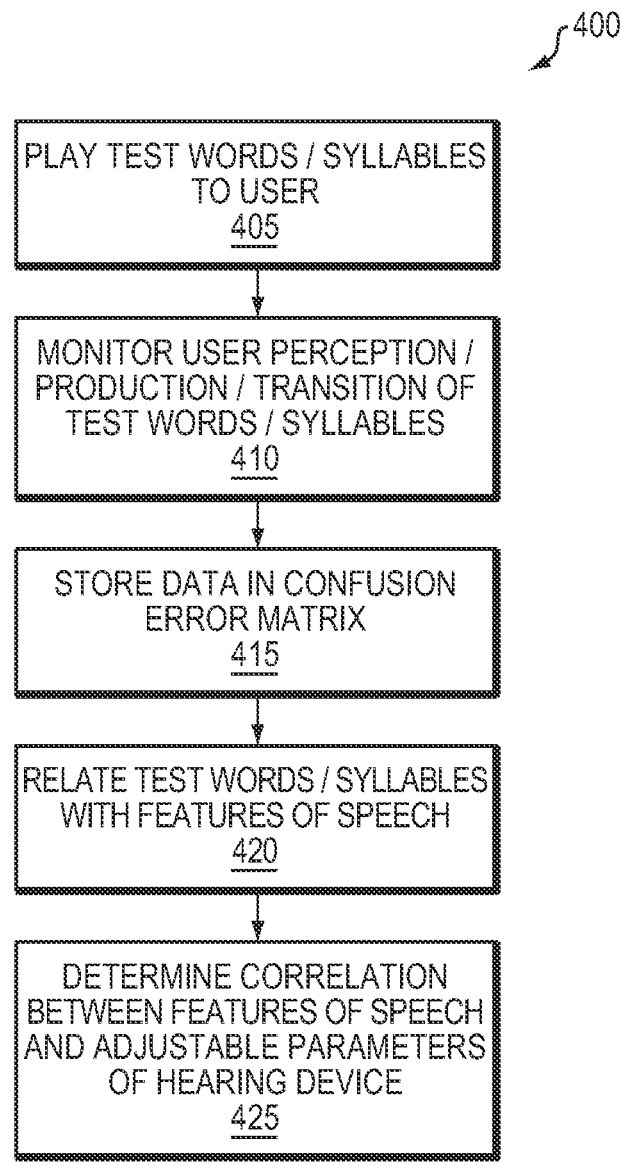
FIG. 4 is a flow chart illustrating a method of determining relationships between distinctive features of speech and adjustable parameters of hearing enhancement systems in accordance with the inventive arrangements disclosed herein.

FIG. 4 is a flow chart illustrating a method 400 of determining relationships between features of speech and adjustable parameters of hearing devices in accordance with the inventive arrangements disclosed herein. The method 400 can begin in a state where a hearing device worn by a user is to be tuned. In accordance with one aspect of the present invention, the user has already undergone an adjustment period of using the hearing device. For example, as the method 400 is directed to determining relationships between distinctive features of speech and parameters of a hearing device, it may be desirable to test a user who has already had ample time to physically adjust to wearing a hearing device.

The method 400 can begin in step 405 where a set of test words and/or syllables can be played to the user. In step 410, the user's understanding of the test audio can be monitored. That is, the user's perception of what is heard, production of what was heard, and transition can be monitored. For example, in one aspect of the present invention, the user can repeat any perceived audio aloud. As noted, the user responses can be automatically recognized by a speech recognition system or can be noted by a human monitor. In another aspect, the user can select an option from a visual interface indicating what the user perceived as the test audio.

In step 415, the test data can be recorded into the confusion error matrix. For example, the word played to the user can be stored in the CEM, whether as text, audio, and/or both. Similarly, the user responses can be stored as audio, textual representations of audio or speech recognized text, and/or both. Accordingly, the CEM can maintain a log of test words/syllables and matching user responses. It should be appreciated by those skilled in the art that the steps 405, 410 and 415 can be repeated for individual users such that portions of test audio can be played sequentially to a user until completion of a test.

After obtaining a suitable amount of test data, analysis can begin. In step 420, each error on the CEM can be analyzed in terms of a set of distinctive features represented by the test word or syllable. The various test words and/or syllables can be related or associated with the features of speech for which each such word and/or syllable is to test. Accordingly, a determination can be made as to whether the user was able to accurately perceive each of the distinctive features as indicated by the user's response. The present invention contemplates detecting both the user's perception of test audio as well as the user's speech production, for example in the case where the user responds by speaking back the test audio that is perceived. Mispronunciations by the user can serve as an indicator that one or more of the distinctive features represented by the mispronounced word or syllable are not being perceived correctly despite the use of the hearing device. Thus, either one or both methods can be used to determine the distinctive features that are perceived correctly and those that are not.

In step 425, correlations between features of speech and adjustable parameters of a hearing device can be determined. For example, such correlations can be determined through an empirical, iterative process where different parameters of hearing devices are altered in serial fashion to determine whether any improvements in the user's perception and/or production result. Accordingly, strategies for altering parameters of a hearing device can be formulated based upon the CEM determined from the user's test session or during the test session.

In illustration, studies have shown that with respect to the distinctive features referred to as grave sounds, such sounds are characterized by a predominance of energy in the low frequency range of speech. Acute sounds, on the other hand, are characterized by energy in the high frequency range of speech. Accordingly, test words and/or syllables representing grave or acute sounds can be labeled as such. When a word exhibiting a grave or acute feature is misrecognized by a user, the parameters of the hearing device that affect the capability of the hearing device to accurately portray high or low frequencies of speech, as the case may be, can be altered. Thus, such parameters can be associated with the misrecognition of acute and/or grave features by a user. Similarly, interrupted sounds are those that have a sudden onset, whereas continuant sounds have a more gradual onset. Users who are not able to adequately discriminate this contrast may benefit from adjustments to device settings that enhance such a contrast.

According to one embodiment of the present invention, Modeling Field Theory (MFT) can be used to determine relationships between operational parameters of hearing devices and the recognition and/or production of distinctive features. MFT has the ability to handle combinatorial complexity issues that exist in the hearing device domain. MFT, as advanced by Perlovsky, combines a priori knowledge representation with learning and fuzzy logic techniques to represent intellect. The mind operates through a combination of complicated a priori knowledge or experience with learning. The optimization of the CI sensor map strategy mimics this type of behavior since the tuning parameters may have different effects on different users.

Still, other computational methods can be used including, but not limited to, genetic algorithms, neural networks, fuzzy logic, and the like. Accordingly, the inventive arrangements disclosed herein are not limited to the use of a particular technique for formulating strategies for adjusting operational parameters of hearing devices based upon speech, or for determining relationships between operational parameters of hearing devices and recognition and/or perception of features of speech.

FIG. 5A is a table 500 listing examples of common operational parameters of hearing devices that can be modified through the use of a suitable control system, such as a computer or information processing system having appropriate software for programming such devices. FIG. 5B is a table 505 illustrating further operational parameters of hearing devices that can be modified using an appropriate control system. Accordingly, through an iterative testing process where a sampling of individuals are tested, relationships between test words, and therefore associated features of speech, and operational parameters of hearing devices can be established. By recognizing such relationships, strategies for improving the performance of a hearing device can be formulated based upon the CEM of a user undergoing testing. As such, hearing devices can be tuned based upon speech rather than tones.

Figure 6:
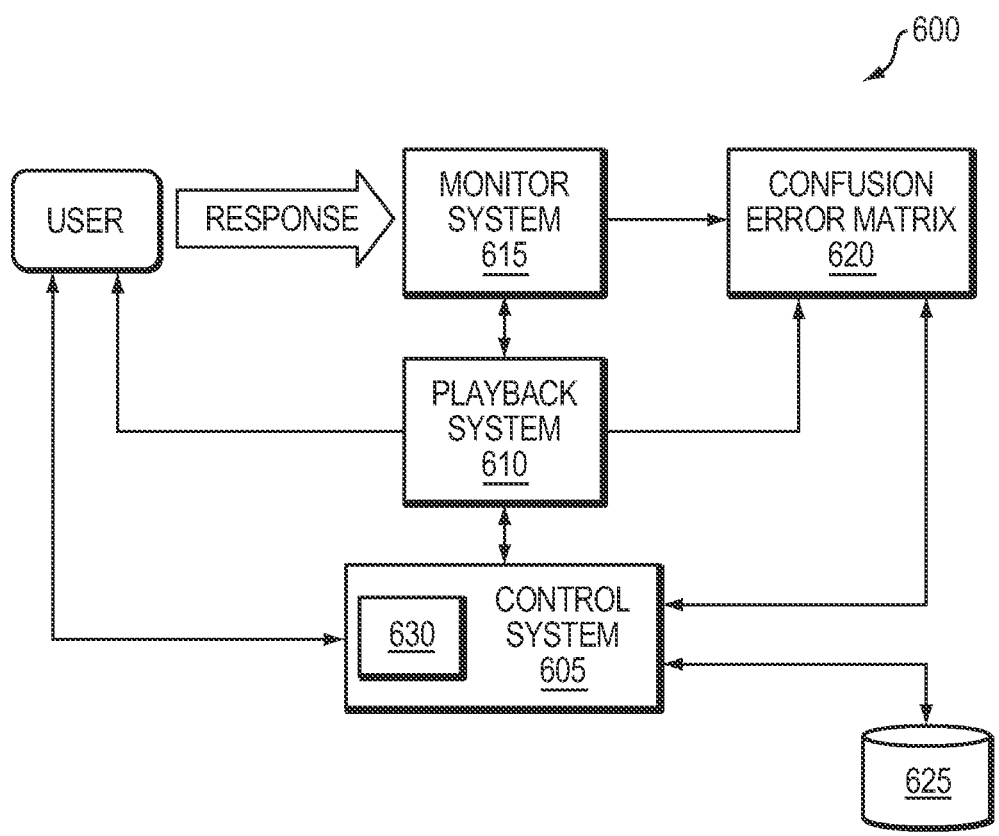
FIG. 6 is a schematic diagram illustrating an exemplary system for determining a mapping for a hearing enhancement system in accordance with the inventive arrangements disclosed herein.

FIG. 6 is a schematic diagram illustrating an exemplary system 600 for determining a mapping for a hearing device in accordance with the inventive arrangements disclosed herein. As shown, the system 600 can include a control system 605, a playback system 610, and a monitor system 615. The system 600 further can include a CEM 620 and a feature to map parameter knowledge base (knowledge base) 625.

The playback system 610 can be similar to the playback system as described with reference to FIG. 1. The playback system 610 can play audio renditions of test words and/or syllables and can be directly connected to the user's hearing device. Still, the playback system 610 can play words and/or syllables aloud without a direct connection to the hearing device.

The monitor system 615 also can be similar to the monitor system of FIG. 1. Notably, the playback system 610 and the monitor system 615 can be communicatively linked thereby facilitating operation in a coordinated and/or synchronized manner. For example, in one embodiment, the playback system 610 can present a next stimulus only after the response to the previous stimulus has been recorded. The monitor system 615 can include a visual interface allowing users to select visual responses corresponding to the played test audio, for example various correct and incorrect textual representations of the played test audio. The monitor system 615 also can be a speech recognition system or a human monitor.

The CEM 620 can store a listing of played audio along with user responses to each test word and/or syllable. The knowledge base 625 can include one or more strategies for improving the performance of a hearing device as determined through iteration of the method of FIG. 6. The knowledge base 625 can be cross-referenced with the CEM 620, allowing a mapping for the user's hearing device to be developed in accordance with the application of one or more strategies as determined from the CEM 620 during testing. The strategies can specify which operational parameters of the hearing device are to be modified based upon errors noted in the CEM 620 determined in the user's test session.

The control system 605 can be a computer and/or information processing system which can coordinate the operation of the components of system 600. The control system 605 can access the CEM 620 being developed in a test session to begin developing an optimized mapping for the hearing device under test. More particularly, based upon the user's responses to test audio, the control system 605 can determine proper parameter settings for the user's hearing device.

In addition to initiating and controlling the operation of each of the components in the system 600, the control system 605 further can be communicatively linked with the hearing device worn by the user. Accordingly, the control system 605 can provide an interface through which modifications to the user's hearing device can be implemented, either under the control of test personnel such as an audiologist, or automatically under programmatic control based upon the user's resulting CEM 620. For example, the mapping developed by the control system 605 can be loaded in to the hearing device under test.

While the system 600 can be implemented in any of a variety of different configurations, including the use of individual components for one or more of the control system 605, the playback system 610, the monitor system 615, the CEM 620, and/or the knowledge base 625, according to another embodiment of the present invention, the components can be included in one or more computer systems having appropriate operational software.

Figure 7:
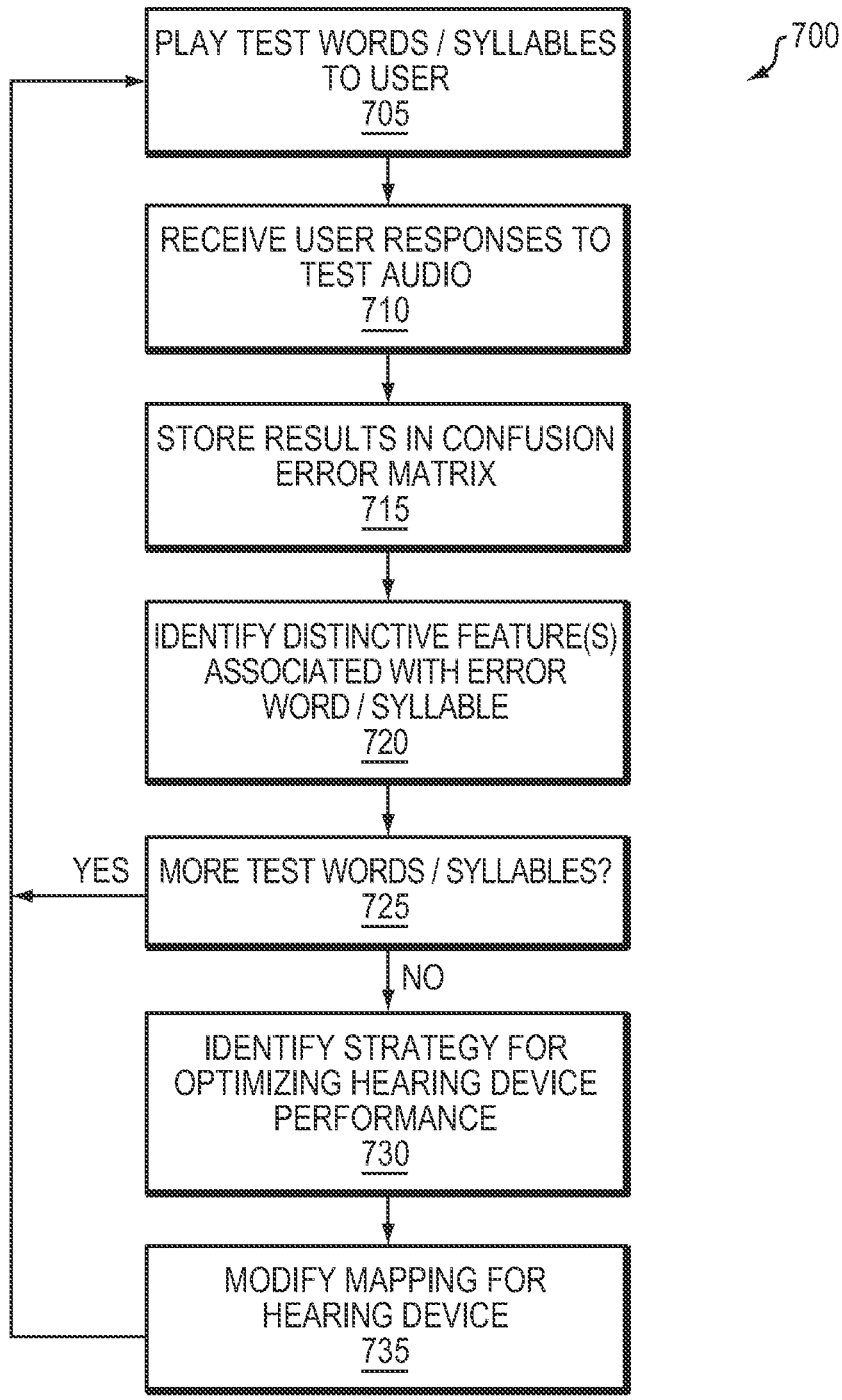
FIG. 7 is a flow chart illustrating a method of determining a mapping for a hearing enhancement system in accordance with the inventive arrangements disclosed herein.

FIG. 7 is a flow chart illustrating a method 700 of determining a mapping for a hearing device in accordance with the inventive arrangements disclosed herein. The method 700 can begin in a state where a user, wearing a hearing device, is undergoing testing to properly configure the hearing device. Accordingly, in step 705, the control system can instruct the playback system to begin playing test audio in a sequential manner.

As noted, the test audio can include, but is not limited to, words and/or syllables including nonsense words and/or syllables. Thus, a single word and/or syllable can be played. As portions of test audio are played, entries corresponding to the test audio can be made in the CEM indicating which word or syllable was played. Alternatively, if the ordering of words and/or syllables is predetermined, the CEM need not include a listing of the words and/or syllables used as the user's responses can be correlated with the predetermined listing of test audio.

In step 710, a user response can be received by the monitor system. The user response can indicate the user's perception of what was heard. If the monitor system is visual, as each word and/or syllable is played, possible solutions can be displayed upon a display screen. For example, if the playback system played the word "Sam", possible selections could include the correct choice "Sam" and an incorrect choice of "sham". The user chooses the selection corresponding to the user's understanding or ability to perceive the test audio.

In another embodiment, the user could be asked to repeat the test audio. In that case the monitor system can be implemented as a speech recognition system for recognizing the user's responses. Still, as noted, the monitor can be a human being annotating each user's response to the ordered set of test words and/or syllables. In any event, it should be appreciated that depending upon the particular configuration of the system used, a completely automated process is contemplated.

In step 715, the user's response can be stored in the CEM. The user's response can be matched to the test audio that was played to illicit the user response. It should be appreciated that, if so configured, the CEM can include text representations of test audio and user responses, recorded audio representations of test audio and user responses, or any combination thereof.

In step 720, the distinctive feature or features represented by the portion of test audio can be identified. For example, if the test word exhibits grave sound features, the word can be annotated as such. In step 725, a determination can be made as to whether additional test words and/or syllables remain to be played. If so, the method can loop back to step 705 to repeat as necessary. If not, the method can continue to step 730. It should be appreciated that samples can be collected and a batch type of analysis can be run at the completion of the testing rather than as the testing is performed.

In step 730, based upon the knowledge base, a strategy for adjusting the hearing device to improve the performance of the hearing device with respect to the distinctive feature(s) can be identified. As noted, the strategy can specify one or more operational parameters of the hearing device to be changed to correct for the perceived hearing deficiency. Notably, the implementation of strategies can be limited to only those cases where the user misrecognizes a test word or syllable.

For example, if test words having grave sound features were misrecognized, a strategy directed at correcting such misperceptions can be identified. As grave sound features are characterized by a predominance of energy in the low frequency range of speech, the strategy implemented can include adjusting parameters of the hearing device that affect the way in which low frequencies are processed. For instance, the strategy can specify that the mapping should be updated so that the gain of a channel responsible for low frequencies is increased. In another embodiment, the frequency ranges of each channel of the hearing device can be varied.

It should be appreciated that the various strategies can be formulated to interact with one another. That is, the strategies can be implemented based upon an entire history of recognized and misrecognized test audio rather than only a single test word or syllable. As the nature of a user's hearing is non-linear, the strategies further can be tailored to adjust more than a single parameter as well as offset the adjustment of one parameter with the adjusting (i.e. raising or lowering) of another. In step 735, a mapping being developed for the hearing device under test can be modified. In particular, a mapping, whether a new mapping or an existing mapping, for the hearing device can be updated according to the specified strategy.

It should be appreciated, however, that the method 700 can be repeated as necessary to further develop a mapping for the hearing device. According to one aspect of the present invention, particular test words and/or syllables can be replayed, rather than the entire test set, depending upon which strategies are initiated to further fine tune the mapping. Once the mapping is developed, the mapping can be loaded into the hearing device.

Those skilled in the art will recognize that the inventive arrangements disclosed herein can be applied to a variety of different languages. For example, to account for the importance of various distinctive features from language to language, each strategy can include one or more weighted parameters specifying the degree to which each hearing device parameter is to be modified for a particular language. The strategies of such a multi-lingual test system further can specify subsets of one or more hearing device parameters that may be adjusted for one language but not for another language. Accordingly, when a test system is started, the system can be configured to operate or conduct tests for an operator specified language. Thus, test audio also can be stored and played for any of a variety of different languages.

The present invention also can be used to overcome hearing device performance issues caused by the placement of the device within a user. For example, the placement of a cochlear implant within a user can vary from user to user. The tuning method described herein can improve performance caused, at least in part, by the particular placement of cochlear implant.

Still, the present invention can be used to adjust, optimize, compensate, or model communication channels, whether an entire communication system, particular equipment, etc. Thus, by determining which distinctive features of speech are misperceived or are difficult to identify after the test audio has been played through the channel, the communication channel can be modeled. The distinctive features of speech can be correlated to various parameters and/or settings of the communication channel for purposes of adjusting or tuning the channel for increased clarity.

For example, the present invention can be used to characterize the acoustic environment resulting from a structure such as a building or other architectural work. That is, the effects of the acoustic and/or physical environment in which the speaker and/or listener is located can be included as part of the communication system being modeled. In another example, the present invention can be used to characterize and/or compensate for an underwater acoustic environment. In yet another example, the present invention can be used to model and/or adjust a communication channel or system to accommodate for aviation effects such as effects on hearing resulting from increased G-forces, the wearing of a mask by a listener and/or speaker, or the Lombard effect. The present invention also can be used to characterize and compensate for changes in a user's hearing or speech as a result of stress, fatigue, or the user being engaged in deception.

The present invention can be realized in hardware, software, or a combination of hardware and software. The present invention can be realized in a centralized fashion in one computer system, or in a distributed fashion where different elements are spread across several interconnected computer systems. Any kind of computer system or other apparatus adapted for carrying out the methods described herein is suited. A typical combination of hardware and software can be a general purpose computer system with a computer program that, when being loaded and executed, controls the computer system such that it carries out the methods described herein.

The present invention also can be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

In the embodiments described above, the software may be configured to run on any computer or workstation such as a PC or PC-compatible machine, an Apple Macintosh, a Sun workstation, etc. In general, any device can be used as long as it is able to perform all of the functions and capabilities described herein. The particular type of computer or workstation is not central to the invention, nor is the configuration, location, or design of a database, which may be flat-file, relational, or object-oriented, and may include one or more physical and/or logical components.

The servers may include a network interface continuously connected to the network, and thus support numerous geographically dispersed users and applications. In a typical implementation, the network interface and the other internal components of the servers intercommunicate over a main bi-directional bus. The main sequence of instructions effectuating the functions of the invention and facilitating interaction among clients, servers and a network, can reside on a mass-storage device (such as a hard disk or optical storage unit) as well as in a main system memory during operation. Execution of these instructions and effectuation of the functions of the invention is accomplished by a central-processing unit ("CPU").

A group of functional modules that control the operation of the CPU and effectuate the operations of the invention as described above can be located in system memory (on the server or on a separate machine, as desired). An operating system directs the execution of low-level, basic system functions such as memory allocation, file management, and operation of mass storage devices. At a higher level, a control block, implemented as a series of stored instructions, responds to client-originated access requests by retrieving the user-specific profile and applying the one or more rules as described above.

Communication may take place via any media such as standard telephone lines, LAN or WAN links (e.g., T1, T3, 56 kb, X.25), broadband connections (ISDN, Frame Relay, ATM), wireless links, and so on. Preferably, the network can carry TCP/IP protocol communications, and HTTP/HTTPS requests made by the client and the connection between the client and the server can be communicated over such TCP/IP networks. The type of network is not a limitation, however, and any suitable network may be used. Typical examples of networks that can serve as the communications network include a wireless or wired Ethernet-based intranet, a local or wide-area network (LAN or WAN), and/or the global communications network known as the Internet, which may accommodate many different communications media and protocols.

While there have been described herein what are to be considered exemplary and preferred embodiments of the present invention, other modifications of the invention will become apparent to those skilled in the art from the teachings herein. The particular methods of manufacture and geometries disclosed herein are exemplary in nature and are not to be considered limiting. It is therefore desired to be secured in the appended claims all such modifications as fall within the spirit and scope of the invention. Accordingly, what is desired to be secured by Letters Patent is the invention as defined and differentiated in the following claims, and all equivalents.

What is claimed is:

1. A system for tuning a hearing device, the system comprising:
  a first transmitter for sending a test signal to a model of the hearing device;
  an encoder for encoding the test signal using the model of the hearing device, wherein the model identifies a type of the hearing device being tested;
  a processor for setting a parameter of the model, wherein the parameter is based at least on a measured response;
  a second transmitter for sending the encoded test signal to the hearing device associated with a user;
  a receiver for receiving a user response, wherein the user response is provided in response to the encoded signal; and
  a comparison module for comparing the user response to the test signal.

2. The system of claim 1, further comprising a test set generator for generating a test signal.

3. The system of claim 2, wherein the test set generator and the comparison module are located remote from the hearing device.

4. The system of claim 3, wherein the signal encoder and the model of the hearing device are located remote from the hearing device.

5. The system of claim 1, further comprising an adjustment module for selecting an operational parameter of the hearing device based at least on a comparison of the user response and the test signal.

6. The system of claim 5, wherein the second transmitter transmits the operational parameter to the hearing device.

7. The system of claim 5, wherein the encoded test signal comprises at least one distinctive feature of speech.

8. The system of claim 7, wherein the at least one distinctive feature of speech comprises at least one of a fundamental source feature, a secondary consonantal source feature, and a resonance feature.

9. The system of claim 7, further comprising an association module for associating the operational parameter of the hearing device with the at least one distinctive feature of speech.

10. The system of claim 1, wherein the encoded test signal is sent over a network.

11. A digital hearing device comprising the system of claim 1.

12. A method of tuning a hearing device, the method comprising the steps of:
sending a test signal to a model of the hearing device;
encoding the test signal using the model of the hearing device, wherein the model identifies a type of the hearing device being tested;
sending the encoded test signal to the hearing device associated with a user;
receiving a user response to the encoded test signal;
comparing the user response with the test signal; and
sending at least one operational parameter to the hearing device based at least on the comparison.

13. The method of claim 12, further comprising the step of selecting a test signal.

14. The method of claim 12, wherein the test signal comprises at least one feature of speech.

15. The method of claim 14, wherein the encoding step comprises digitizing the at least one feature of speech.

16. The method of claim 14, wherein the encoding step comprises adjusting a characteristic of the feature of speech.

17. The method of claim 16, wherein the characteristic of the feature of speech comprises at least one of a fundamental source feature, a secondary consonantal source feature, and a resonance feature.

18. The method of claim 12, wherein the test signal comprises an electrical signal corresponding to a stimuli comprising at least one feature of speech.

19. The method of claim 16, further comprising the step of associating the operational parameter of the hearing device with the at least one feature of speech.

20. The method of claim 12, wherein the encoded test signal is sent over a network.

21. The method of claim 20, wherein the network is TCP/IP enabled.

22. The method of claim 12, wherein the model of the hearing device is located remote from the hearing device.

23. The method of claim 12, wherein the model of the hearing device is collocated with the hearing device.

24. The method of claim 14, further comprising the step of receiving at the hearing device the encoded test signal and processing the encoded test signal.

25. The method of claim 24, wherein the processing step comprises reproducing the at least one feature of speech.

26. An article of manufacture comprising computer-readable program instructions that, when executed by at least one processor, perform a method for tuning a hearing device, the method comprising:
sending a test signal to a model of the hearing device;
encoding the test signal using the model of the hearing device, wherein the model identifies a type of the hearing device being tested;
sending the encoded test signal to the hearing device associated with a user;
receiving a user response to the encoded test signal;
comparing the user response with the test signal; and
sending at least one operational parameter to the hearing device based at least on the comparison.

\* \* \* \* \*